United States Patent [19]

Bermes et al.

[11] Patent Number: 5,424,403

[45] Date of Patent: Jun. 13, 1995

[54] PREPARATION OF AMINOAZO DYES

[75] Inventors: Rudolf Bermes, Ludwigshafen; Heinz Keilhauer, Birkenheide, both of Germany

[73] Assignee: BASF Aktiengesellschaft, Ludwigshafen, Germany

[21] Appl. No.: 246,750

[22] Filed: May 20, 1994

[51] Int. Cl.[6] .............................. C09B 43/00
[52] U.S. Cl. .................. 534/599; 534/593; 534/845; 534/851
[58] Field of Search .............. 534/599, 593, 845, 851; 564/394

[56]  References Cited

U.S. PATENT DOCUMENTS

| | | | |
|---|---|---|---|
| 1,042,198 | 10/1912 | Cantor | 534/845 X |
| 1,483,797 | 2/1924 | Green et al. | 8/529 |
| 1,483,798 | 2/1924 | Green et al. | 534/845 X |
| 2,088,327 | 7/1937 | Knight | 534/845 |
| 2,112,919 | 4/1938 | Mendoza et al. | 534/851 X |

FOREIGN PATENT DOCUMENTS 131860  6/1902  Germany .............................. 534/599

OTHER PUBLICATIONS

Houben-Weyl, Methoden der Organischen Chemie, 4th edition, vol. 10/3, p. 242, 1965.
Colour Index, 3rd edition, vol. 4, C.I. Nos. 13010, 13130 and 13200, 1971.
Loeffler et al., Chemical Abstracts, 106:34619 (1986).
Arsac, Chemical Abstracts, 94:4948 (1980).

*Primary Examiner*—Mary C. Lee
*Assistant Examiner*—Fiona T. Powers
*Attorney, Agent, or Firm*—Oblon, Spivak, McClelland, Maier, & Neustadt

[57]  ABSTRACT

Aminoazo dyes are prepared from the corresponding N-sulfomethylated aminoazo dyes by aqueous acid hydrolysis in the presence of amidosulfuric acid, urea or mixtures thereof.

5 Claims, No Drawings

PREPARATION OF AMINOAZO DYES

The present invention relates to a novel process for preparing aminoazo dyes by aqueous acidic hydrolysis of the corresponding N-sulfomethylated aminoazo dyes.

The hydrolysis of N-sulfomethylated aminoazo dyes is already known from Houben-Weyl, Methoden der Organischen Chemie, 4th edition, volume 10/3, page 242, 1965.

However, it has been found that the methods described there have disadvantages. For instance, the rate of hydrolysis is relatively low. Moreover, the aminoazo dyes are obtained in unsatisfactory yield and purity.

It is an object of the present invention to provide a novel process for the acidic hydrolysis of N-sulfomethylated aminoazo dyes whereby the target products are obtained in high yield and purity. Also, the hydrolysis rate shall be high.

We have found that this object is achieved by a process for preparing aminoazo dyes of the formula I

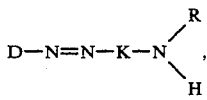  (I)

where
D is substituted or unsubstituted phenyl,
K is substituted or unsubstituted phenylene, and
R is hydrogen or $C_1$-$C_4$-alkyl, by aqueous acidic hydrolysis of sulfomethylated aminoazo dyes of the formula II

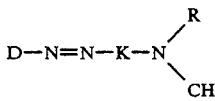  (II)

where D, K and R are each as defined above, or salts thereof, which comprises hydrolyzing in the presence of amidosulfuric acid, urea or mixtures thereof.

The hydrolysis can be carried out with the sulfomethylated aminoazo dyes of the formula II either in the form of free acids or in the form of their salts.

Suitable salts include for example the alkali or alkaline earth metal salts, such as the lithium, sodium, potassium, magnesium or calcium salts, or ammonium salts.

The use of the sodium or potassium salts is preferred.

Any alkyl appearing in the abovementioned formulae I and II may be straight-chain or branched.

In substituted radicals D and K, the number of substituents is generally from 1 to 3.

Suitable substituents include for example $C_1$-$C_4$-alkyl, $C_1$-$C_4$-alkoxy, halogen, nitro, hydroxysulfonyl, carboxyl, cyano or $C_1$-$C_4$-alkanoylamino.

$C_1$-$C_4$-alkyl radicals include for example methyl, ethyl, propyl, isopropyl, butyl, isobutyl or sec-butyl.

$C_1$-$C_4$-alkoxy radicals include for example methoxy, ethoxy, propoxy, isopropoxy, butoxy, isobutoxy or sec-butoxy.

Halogen is for example fluorine, chlorine or bromine.

$C_1$-$C_4$-alkylamino is for example formylamino, acetylamino, propionylamino, butyrylamino or isobutyrylamino.

Preference is given to a process for preparing aminoazo dyes of the formula I where R is hydrogen.

Preference is further given to a process for preparing aminoazo dyes of the formula I where D is phenyl or $C_1$-$C_4$-alkyl-, halogen-, nitro-, hydroxysulfonylor carboxyl-substituted phenyl.

Preference is further given to a process for preparing aminoazo dyes of the formula I where K is phenylene or $C_1$-$C_4$-alkyl-, $C_1$-$C_4$-alkoxy- or halogen-substituted phenylene.

The hydrolysis of the sulfomethylated aminoazo dyes of the formula II takes place in an aqueous acidic medium. Suitable aqueous acidic media include for example aqueous solutions of inorganic or organic acids, for example halohydric acids, such as hydrochloric acid or hydrobromic acid, sulfuric acid, amidosulfuric acid, phosphoric acid, formic acid, benzenesulfonic acid or toluenesulfonic acid.

The acid concentration in the aqueous acidic medium is usually from 0.5 to 15% by weight, preferably from 1 to 10% by weight, in each case based on the weight of the reaction medium.

The amount of aqueous acidic reaction medium is not critical, but care should be taken to ensure that the reaction mixture remains stirrable.

According to the invention, the novel process is carried out in the presence of amidosulfuric acid, urea or mixtures thereof. These reagents are advantageously used in an amount from 0.5 to 5 mol, preferably from 1 to 2.5 mol and in particular from 1 to 2 mol, per mole of sulfomethylated aminoazo dye of the formula II.

The use of amidosulfuric acid is preferred.

The amidosulfuric acid can be used at one and the same time as acid component for the aqueous acidic medium and as hydrolysis improver. The abovementioned proportions must be taken into account.

The process of the invention is generally carried out at a temperature from 60 to 120° C., preferably from 70 to 95° C.

The hydrolysis generally takes only a short time, usually from 15 to 60 minutes.

Preference is given to a process starting not from the isolated sulfomethylated aminoazo dye of the formula II but from its as-obtained synthesis mixture. Accordingly, first an amine of the formula III

  (III), where D is as defined above, is diazotized in a conventional manner and coupled with a sulfomethylated coupling component of the formula IV

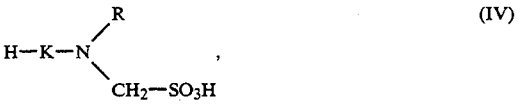  (IV)

where K and R are each as defined above. The resulting mixture can then be directly subjected to acid hydrolysis as described above.

In an advantageous form of the novel process, an aqueous acidic solution or suspension of the sulfomethylated aminoazo dye of the formula II is admixed with amidosulfuric acid, urea or a mixture thereof and heated to the abovementioned temperature with stirring. On completion of the hydrolysis, which can be monitored for example by chromatography, the reaction mixture is cooled down and the aminoazo dye of the formula I, which will usually be present in solid form, is isolated, for example by filtering off with suction, washing with water and drying.

The novel process makes it possible to prepare the aminoazo dyes of the formula I in high yield. Their purity is also very good.

The compounds I of the formula I obtainable by means of the process according to the invention have dye characteristics themselves and also are useful intermediates for preparing further substituted dyes, for example polyazo dyes.

The Examples which follow illustrate the invention.

EXAMPLE 1

173 g of sulfanilic acid were diazotized in a conventional manner in 1000 ml of ice-water at pH 1.3 in the presence of 60 g of concentrated sulfuric acid using 69 g of sodium nitrite. The stirred suspension was rendered less acid with 100 g of sodium bicarbonate and admixed with 220 g of sodium anilinomethanesulfonate. The coupling was completed overnight. The pH of the mixture was 5.7. Then 100 g of amidosulfuric acid and 100 g of concentrated sulfuric acid diluted with a little ice were added, and the batch was heated to 95° C. and stirred at that temperature for 15 min. Thereafter the batch was cooled down to room temperature and the precipitate was filtered off with suction. After washing with 3000 ml of water, the filter cake was dried at 80° C. to leave 256 g of 4'-aminoazobenzene-4-sulfonic acid having a purity of 98.6%.

EXAMPLE 2

Example 1 was repeated with the amidosulfuric acid replaced by 100 g of concentrated sulfuric acid. Two hours' hydrolysis at 95° C. give only 220 g of the dye having a purity of only 88.0%.

EXAMPLE 3

The coupling reaction of Example 1 was repeated with only 0.6 times the amount of the reactants. Then the resulting coupling mixture was divided into 3 equal parts.

a) One part was admixed with 20 g of amidosulfuric acid and 20 g of concentrated sulfuric acid and brought to 95° C. to eliminate the sulfomethyl radical. This gave 44.2 g of 4'-aminoazobenzene-4-sulfonic acid having a purity of 97.6%.

b) Part two was admixed with 20 g of urea and 30 parts of concentrated sulfuric acid, affording 41.1 g of the dye having a purity of 98.7%.

c) Part three was admixed with only 30 g of concentrated sulfuric acid. In this case the yield was 37.2 g of dye having a purity of 91.9%.

EXAMPLE 4

The coupling reaction of Example 1 was repeated with only 0.5 times the amount of each of the reactants. The resulting coupling mixture was admixed with 200 g of formic acid and 50 g of amidosulfuric acid and stirred at 95° C. for 1 h. Workup gave 101.2 g of 4'-aminoazobenzene-4-sulfonic acid having a purity of 96.9%.

EXAMPLE 5

Example 4 was repeated with only 200 g of formic acid to eliminate the sulfomethyl radical. The yield was only 78.8 g of dye having a purity of only 79.8%.

EXAMPLE 6

Example 4 was repeated with the amidosulfuric acid replaced by the same amount of urea. The yield was 103.8 g of dye having a purity of 97.3%.

EXAMPLE 7

Example 4 was repeated with the formic acid replaced by the same amount of benzenesulfonic acid, affording 104.8 g of dye having a purity of 96.0%.

EXAMPLE 8

Example 7 was repeated without amidosulfuric acid. The yield was 96.0 g of dye having a purity of 93.0%.

EXAMPLE 9

Example 1 was repeated with the sulfanilic acid replaced by an equivalent amount of 2-aminotoluene-5sulfonic acid, affording 250 g of 4'-amino-2-methylazobenzene-4-sulfonic acid having a purity of 98%.

EXAMPLE 10

Example 9 was repeated with the sodium anilinomethanesulfonate replaced by an equivalent amount of sodium o-toluidinomethanesulfonate and–in order that the crystal mush formed in the course of the hydrolysis remained stirrable–the amount of water increased to such an extent that the batch volume was about 10 l. This gave 262 g of 4'-amino-3',2-dimethylazobenzene-4-sulfonic acid having a purity of 96.9%.

EXAMPLE 11

137 g of 3-aminobenzoic acid and 90 g of 50% strength sodium hydroxide solution were dissolved in 1000 ml of water and mixed with a solution of 70 g of sodium nitrite in 300 ml of water. 500 g of ice were stirred in and this solution was added at from 0 to 5° C. over 30 min with external cooling to a stirred mixture of 135 g of concentrated sulfuric acid and 500 g of ice. After 2 h the excess nitrite was destroyed with a little amidosulfuric acid, the diazonium salt solution was filtered and added to a suspension of 240 g of sodium o-anisidinomethanesulfonate in 500 ml of water to which 220 g of sodium bicarbonate had been added. Stirring was continued overnight, at which point 100 g of amidosulfuric acid and 100 g of concentrated sulfuric acid were added to the reaction mixture and stirring was continued at 95° C. for 1 h. The workup gave 254 g of 4'-amino-3'-methoxyazobenzene-3-carboxylic acid having a purity of 97.2%.

EXAMPLE 12

Example 1 was repeated with the sulfanilic acid replaced by an equivalent amount of 4-amino-2,5-dichlorobenzenesulfonic acid, affording 310 g of 4'-amino-2,5-dichlorobenzene-4-sulfonic acid having a purity of 97.7%.

EXAMPLE 13

Example 1 was repeated with the sodium anilinomethanesulfonate replaced by an equivalent amount of N-(hydroxysulfonylmethyl)-3-chloroaniline and the subsequent hydrolysis being carried out at 95° C. with 250 g of amidosulfuric acid. Filtration with suction, washing and drying left 209 g of 2'-chloro-4'-aminoazobenzene-4-sulfonic acid having a purity of 99.3%.

We claim:

1. A process for preparing aminoazo dyes of the formula I

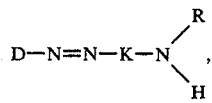

where
D is substituted or unsubstituted phenyl,
K is substituted or unsubstituted phenylene, and
R is hydrogen or $C_1$-$C_4$-alkyl, by aqueous acidic hydrolysis of sulfomethylated aminoazo dyes of the formula II

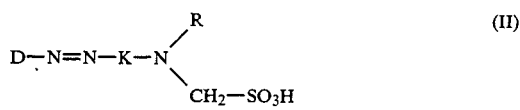

where D, K and R are each as defined above, or salts thereof, which comprises hydrolyzing in the presence of amidosulfuric acid, urea or mixtures thereof.

2. A process as claimed in claim 1, wherein R is hydrogen.

3. A process as claimed in claim 1, wherein the hydrolysis is carried out at from 60 to 120° C.

4. A process as claimed in claim 1, wherein from 0.5 to 5 mol of amidosulfuric acid, urea or mixtures thereof are used per mole of sulfomethylated aminoazo dye of the formula II.

5. A process as claimed in claim 1, wherein the hydrolysis is carried out in the presence of amidosulfuric acid.

* * * * *

UNITED STATES PATENT AND TRADEMARK OFFICE
CERTIFICATE OF CORRECTION

PATENT NO. : 5,424,403
DATED : June 13, 1995
INVENTOR(S) : Rudolf Bermes et al.

It is certified that error appears in the above-indentified patent and that said Letters Patent is hereby corrected as shown below:

COL.  LINE

4,   Example 12, lines 56 and 57, please delete "4'-amino-2,5-dichlorobenzene-4-sulfonic" and insert --4'-amino-2,5-dichloroazobenzene-4-sulfonic--.

Signed and Sealed this

Twenty-seventh Day of February, 1996

Attest:

BRUCE LEHMAN

*Attesting Officer*  *Commissioner of Patents and Trademarks*